United States Patent [19]

Krone-Schmidt

[11] Patent Number: 5,282,381

[45] Date of Patent: Feb. 1, 1994

[54] SUPERCRITICAL FLUID CONTAMINATION MONITOR

[75] Inventor: Wilfried Krone-Schmidt, Fullerton, Calif.

[73] Assignee: Hughes Aircraft Company, Los Angeles, Calif.

[21] Appl. No.: 942,017

[22] Filed: Sep. 8, 1992

[51] Int. Cl.$^5$ ............................ B01D 15/00; B01J 39/00
[52] U.S. Cl. ................................ 73/61.41; 73/64.56; 210/96.1; 210/662; 210/746; 324/663; 324/693
[58] Field of Search ............................ 73/61.41, 64.56; 324/663, 693; 210/96.1, 662, 746

[56] References Cited

U.S. PATENT DOCUMENTS

| | | | |
|---|---|---|---|
| 3,159,573 | 12/1964 | Ritchie | 210/96.1 |
| 3,167,949 | 2/1965 | Stenzel et al. | 73/61.72 |
| 3,238,452 | 3/1966 | Schmitt et al. | 73/61.41 |
| 4,299,698 | 11/1981 | Rak et al. | 210/96.1 |
| 4,597,943 | 7/1986 | Sugiyama et al. | 210/96.1 |
| 5,143,696 | 9/1992 | Haas et al. | 324/663 |

*Primary Examiner*—Robert J. Warden
*Assistant Examiner*—L. M. Crawford
*Attorney, Agent, or Firm*—M. E. Lachman; M. W. Sales; W. K. Denson-Low

[57] ABSTRACT

A system and method for detecting the presence of contaminants in supercritical fluid. The system is based upon the use of an absorbent module comprising an absorbent which selectively absorbs the contaminant being measured and wherein the electrical properties (i.e. conductance and/or capacitance) of the absorbent varies depending upon the amount of contaminant absorbed. A sample stream of the supercritical fluid is contacted with the absorbent material. By measuring the electrical properties of the absorbent, contaminant levels are measured and monitored.

11 Claims, 2 Drawing Sheets

SUPERCRITICAL FLUID CONTAMINATION MONITOR

BACKGROUND OF THE INVENTION

1. Field of the Invention

The present invention relates generally to the use of dense phase gases for cleaning and extracting materials. More particularly, the present invention relates to the use of conductance and/or capacitance measurements to detect the presence of contaminants in such dense phase gases and to monitor the amount of contaminants present in the dense fluids as the cleaning or extraction process progresses.

2. Description of Related Art

Conventional solvent-aided cleaning processes are currently under severe scrutiny due to problems with air pollution and ozone depletion. In addition, recent environmental concerns mandate that many of the organic solvents used in these processes be banned or their use severely limited. The use of dense phase gases for cleaning a wide variety of materials has been under investigation as an alternative to the above-mentioned solvent based cleaning processes. A dense phase gas is a gas compressed under either supercritical or subcritical conditions to liquid-like densities. These dense phase gases are also referred to as dense fluids. Unlike organic solvents, such as n-hexane, or 1,1,1-trichloromethane, dense phase gas solvents exhibit unique physical properties such as low surface tension, low viscosity, high diffusivity and variable solute carrying capacity.

The solvent properties of compressed gases are well known, as discussed in U.S. Pat. No. 5,068,040, assigned to the present assignee. In the late 1800's, Hannay and Hogarth found that inorganic salts could be dissolved in supercritical ethanol and ether (J. B. Hannay and H. Hogarth, *J.Prof.Rov.Soc.* (London, 29, p.324, 1897). By the early 1900's, Buchner discovered that the solubility of organics such as naphthalene and phenols in supercritical carbon dioxide increased with pressure (E. A. Buchner, *Z.Physik.Chem.*, 54, p. 665, 1906). Within forty years Francis had established a large solubility database for liquified carbon dioxide which showed that many organic compounds were completely miscible (A. W. Francis, *J.Phys.Chem.*, 58, p. 1099, 1954).

In the 1960's there was much research and use of dense gases in the area of chromatography. Supercritical fluids (SCF) were used as the mobile phase in separating non-volatile chemicals (S. R. Springston and M. Novotny, "Kinetic Optimization of Capillary Supercritical Chromatography using Carbon Dioxide as the Mobile Phase", *CHROMATOGRAPHIA*, Vol. 14, No. 12, p. 679, December 1981). Today the environmental risks and costs associated with conventional solvent-aided separation processes require industry to develop safer and more cost-effective alternatives.

The volume of current literature on solvent-aided separation processes using dense phase carbon dioxide as a solvent is evidence of the extent of industrial research and development in the field. Documented industrial applications utilizing dense fluid cleaning include extraction of oil from soybeans (J. P. Friedrich and G. R. List and A. J. Heakin, "Petroleum-Free Extracts of Oil from Soybeans", *JAOCS*, Vol. 59, No. 7, July 1982), decaffination of coffee (C. Grimmett, *Chem.Ind.*, Vol. 6, p. 228, 1981), extraction of pyridines from coal (T. G. Squires, et al., "Supercritical Solvents. Carbon Dioxide Extraction of Retained Pyridine from Pyridine Extracts of Coal", *FUEL*, Vol. 61, November 1982), extraction of flavorants from hops (R. Vollbrecht, "Extraction of Hops with Supercritical Carbon Dioxide", *Chemistry and Industry*, 19 Jun. 1982), and regenerating absorbents (activated carbon) (M. Modell, "Process for Regenerating Adsorbents with Supercritical Fluids", U.S. Pat. No. 4,124,528, issued 7 Nov. 1978).

Electro-optical devices, lasers and spacecraft assemblies are fabricated from many different types of materials having various internal/external geometrical structures which are generally contaminated with more than one type of contamination. These highly complex and delicate systems are generally classified together as "complex hardware". Conventional cleaning techniques for removing contamination from such complex hardware requires that the hardware be continually cleaned during assembly. The use of supercritical fluids, such as carbon dioxide is particularly well-suited for cleaning such complex hardware.

Supercritical fluid cleaning systems operate at high temperatures and pressures. As a result, real time monitoring of the cleaning process is difficult. In current systems, parts and materials are cleaned or extracted for a period of time and then removed and tested for cleanliness. If the part is still contaminated, it must be reintroduced into the system and recleaned. In order to avoid having to reclean numerous parts, the parts are typically left in the system much longer than necessary to insure adequate cleanliness. This, of course, results in a great deal of unnecessary cleaning, waste of time, and increased costs.

It would be desirable to provide a system for monitoring supercritical fluid cleaning systems to determine when the particular part has been completely cleaned or when the extraction of desired materials has been completed. Such a monitoring system should be simple, efficient and capable of being used to detect a wide variety of contaminants and to monitor a wide variety of cleaning/extraction processes utilizing supercritical fluids.

In addition, minor changes in process parameters can affect the quality of a cleaning or extraction procedure utilizing supercritical fluids. Accordingly, it would be desirable to provide a process for conveniently, quickly and easily measuring the effectiveness of a cleaning and/or extraction procedure. In this way, various process parameters may be rapidly altered to establish the optimum cleaning/extraction conditions. The use of a monitoring system to provide a real-time indication of the degree of cleanliness or extraction in a particular procedure will be helpful in optimizing such procedures.

SUMMARY OF THE INVENTION

In accordance with the present invention, it was discovered that absorbent materials, such as zeolite, may be used as part of a system for detecting the presence of contaminants in a flowing stream of supercritical fluid. The present invention is based upon the discovery that the electrical conductance and/or capacitance of zeolite materials varies depending upon the amount of contaminants which are absorbed therein. This variation in electrical properties is a measurable characteristic which can be used to provide a direct measurement of the accumulation of contaminants in the zeolite.

In accordance with the present invention, a system is provided for detecting the presence of contaminants in a flowing stream of supercritical fluid wherein at least a portion of the supercritical fluid stream is removed to provide a sample stream. The sample stream is passed into a measurement vessel which contains one or more absorbent modules. The absorbent module contains an absorbent material which is capable of selectively absorbing contaminants from the sample stream. A requirement for the absorbent material is that at least one of the electrical properties through the absorbent material varies depending upon the amount of contaminant which is absorbed therein. The capacitance and/or conductance of the absorbent material may be measured continually or at various selected times to provide for monitoring and detection of contaminants in the sample stream.

During supercritical fluid cleaning and/or extraction processes, the amount of removed material, i.e. contaminants, in the flowing stream of supercritical fluid gradually decreases as the process continues. As the amount of contaminants decreases, the change in the amount of contaminants also decreases. Accordingly, monitoring of the change in the amount of contaminants present in the flowing stream of supercritical fluid provides an accurate and reliable real-time indication of the degree of cleanliness or extraction of a particular material. As a feature of the present invention, this change in contaminant levels in the flowing stream of supercritical fluid may be monitored by measuring changes in the electrical properties of absorbent materials used as detectors.

As an additional feature of the present invention, the total amount of contaminants absorbed by an absorbent detector during an extraction or cleaning procedure can be measured to provide an accurate indication of the overall effectiveness of the particular procedure.

As another feature of the present invention, the sample stream of supercritical fluid may be contacted with the absorbent module without requiring conversion of the supercritical fluid into a gaseous state. The ability of the absorbent material to absorb contaminants directly from the sample stream provides a more straight-forward system than such monitoring systems that required expanding the supercritical fluid into a gaseous state, depositing contaminants onto a measurement detector and recompressing the gas to a liquid state.

As a further feature of the present invention, a plurality of absorbent modules having selective absorption characteristics for different contaminants may be used simultaneously to monitor the supercritical fluid for a variety of different contaminants. In addition, a plurality of absorbent modules may be used sequentially during a cleaning or extraction process to monitor different stages of the procedure. For example, the contaminant levels in the supercritical fluid may be high during the early stages of a cleaning or extraction process. In accordance with a feature of the present invention, the sample fluid is sequentially cycled to different absorbent modules as the absorbent modules become saturated with contaminants during the early stages of the process.

As another feature of the present invention, the total amount of contaminants absorbed by the absorbent module may be measured during a particular cleaning or extraction process by comparing the electrical conductance and/or capacitance measured at the beginning and end of the process. This capability to quantitatively measure the amount of contaminants generated during a particular procedure allows one to adjust various process parameters to optimize a particular cleaning and/or extraction procedure.

The above-discussed and many other features and attendant advantages of the present invention will become better understood by reference to the following detailed description when taken in conjunction with the accompanying drawing.

DESCRIPTION OF THE PREFERRED EMBODIMENTS

The monitoring system in accordance with the present invention may be used to monitor contaminants present in a wide variety of supercritical fluids. The present invention is useful in monitoring both cleaning processes and extraction processes. The term "contaminants" is intended to cover both desirable and undesirable materials present in the supercritical fluid. For example, there may be instances in extraction processes when the material extracted into the supercritical fluid may be a desirable product which is isolated and recovered at a later time. For the purposes of this specification, such desirable materials present in the supercritical fluid will be classified and considered together with undesirable materials which are removed during a cleaning process and disposed of.

The following description is directed to an exemplary system where carbon dioxide is used as the supercritical fluid. It will be understood by those skilled in the art that the teachings set forth herein are applicable to any supercritical fluid system wherein the contaminants remain in a non-gaseous form when the supercritical fluid is converted to a gas at reduced pressures. In addition, the terms "supercritical fluid" as used herein is intended to include mixtures of fluids, such as primary supercritical fluid and a non-supercritical co-solvent which enhances cleaning or extracts contaminants which are insoluble in the primary supercritical fluid. The system described below is well-suited for use as a detector in processes for cleaning items to remove organic contaminants which are soluble in supercritical carbon dioxide fluid. However, it will also be understood that this detection/monitoring system may be used for a variety of cleaning and/or extraction processes.

Figure 1:
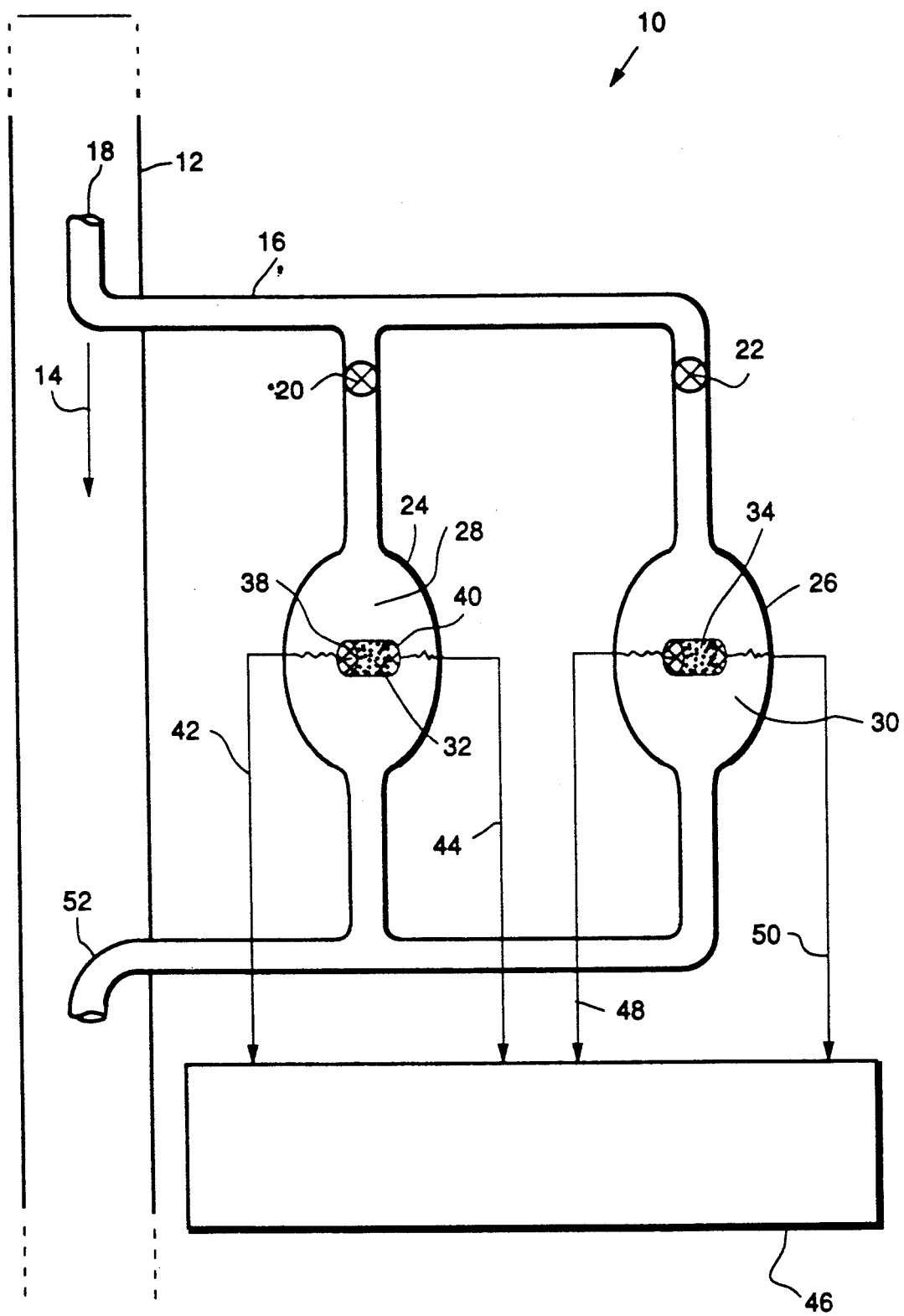
FIG. 1 is a diagrammatic representation of a preferred exemplary monitoring system in accordance with the present invention wherein two absorbent modules are utilized.

A preferred exemplary system in accordance with the present invention is shown partially schematically at 10 in FIG. 1. The system 10 is designed to remove a portion of a stream of carbon dioxide supercritical fluid which is flowing through a conduit 12 as represented by arrow 14. The supercritical fluid is removed from conduit 12 through channel 16 which has an inlet 18. Once the sample stream is removed from conduit 12, the fluid in the sample stream may be in the supricritical state or may be in a non-supercritical state. Valves 20 and 22 are provided for allowing selective introduction of the sample stream into measurement vessels 24 and 26. In accordance with the present invention, only one measurement vessel may be used or numerous vessels may be connected to a single sample conduit 16. The system 10 shown in FIG. includes two measurement vessels 24 and 26 for exemplary purposes only.

Figure 2:
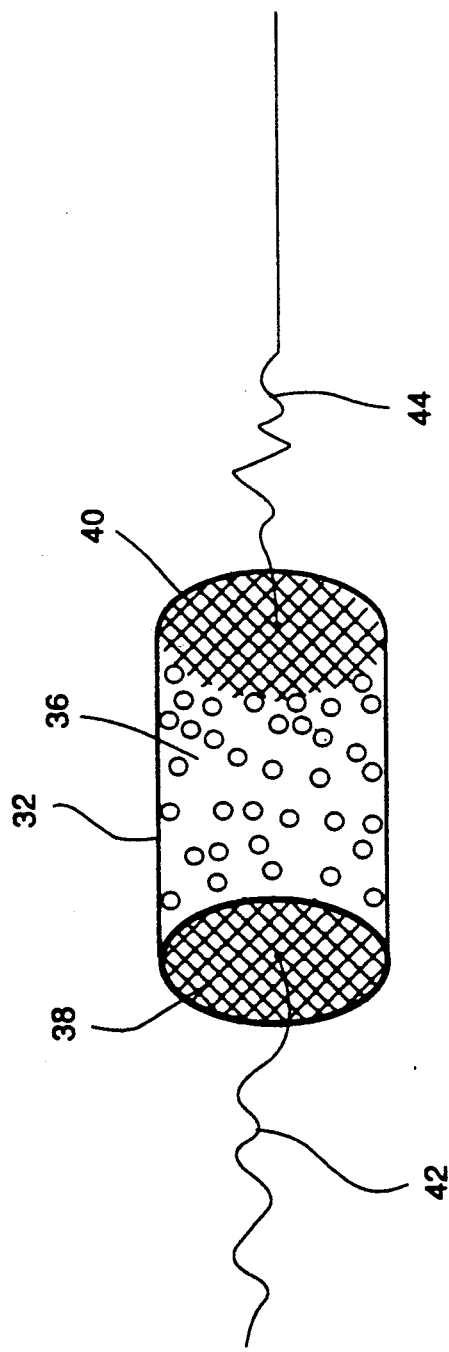
FIG. 2 is a partially schematic detailed representation of a preferred exemplary absorbent module in accordance with the present invention.

The measurement vessels 24 and 26 define measurement zones 28 and 30, respectively, in which absorbent modules 32 and 34 are located. FIG. 2 shows a detailed view of absorbent module 32. The absorbent module 32 is preferably a rod-shaped module which contains an absorbent material which is capable of selectively absorbing contaminants which are present in the sample stream which is introduced into the measurement zone 28 by way of valve 20.

The absorbent material represented pictorially in FIG. 2 as 36 is preferably a zeolite or other absorbent compound which changes its electrical properties depending upon the amount of contaminant absorbed therein. Zeolites are the preferred absorbent material 36 since they are widely available and well known for their ability to selectively absorb a variety of contaminants. Further, the electrical properties of zeolites vary depending upon the amount of contaminant which is absorbed in the zeolite.

Preferably, the absorbent material 36 is a compressed rod of zeolite about the size of a pencil lead, i.e. diameters on the order of 0.3 cm to 1.0 cm. Zeolites for use in accordance with the present invention should have pore sizes on the order of 0.5 angstrom to 130 angstroms, with pore sizes on the order of 5 to 13 angstroms being most preferred. The pore size of the zeolite used as the absorbent material 36 may be varied to provide selective absorption of different contaminants which may be present within the sample stream.

The particular type of zeolite which is used in the absorbent module 32 or 34 is not particularly critical provided that the zeolite is capable of absorbing one or more contaminants of interest and provided that the electrical properties of the zeolite vary when absorption occurs. Suitable zeolites which may be used in accordance with the present invention include chabazite ($Ca_6Al_{12}Si_{24}O_{72}$ $40H_2O$), gmelinite ($(Na_2Ca)_4Al_8Si_{16}O_{48}24H_2O$), erionite ($Ca_{4.5}Al_9Si_{27}O_{72}$ $27H_2O$) and members of the sodalite family either naturally occurring or synthetically produced.

The zeolite used in the absorbent module is preferably a structurally sound material which has been compressed or otherwise fabricated using suitable binders to form a single piece module having a size ranging from between about 0.5 and 2 centimeters. Zeolites in the form of cylinders, disks or cubes are also suitable.

In addition to zeolites, other absorbent materials such as felspathoids may be used as a suitable absorbent material. The zeolite may be synthesized or naturally occurring. The procedures for isolating naturally occurring zeolites and preparing synthetic zeolites are well known and will not be described in detail. Further, a wide variety of zeolite materials in various forms are available commercially.

In accordance with the present invention, electrical contacts, such as electrodes 38 and 40 are connected to the zeolite material to provide a means for measuring the electrical properties through the zeolite material. The electrodes 38 and 40 are preferably a wire mesh made from platinum, gold, copper or other conductive metal typically used as a current collector. Electrodes can be a wire mesh or can be chemically vapor deposited (CVD) directly onto the zeolite. CVD is preferred. The wire mesh electrodes 38 and 40 are connected to wires 42 and 44 respectively. The electrode wires 42 and 44 are connected in turn to an electrical measurement device 46. The absorbent module 34 shown in FIG. 1 is the same as the detailed absorbent module shown in FIG. 2, with lines 48 and 50 connecting their respective electrodes to the electrical measurement device 46. The electrical measurement device 46 may comprise, for example, a high sensitivity ohmmeter, or other commercially available device for such purposes.

During operation, valve 20 is opened to allow a sample stream to flow into the measurement zone 28. Some or all of the contaminants present in the sample stream are absorbed by the absorbent module 32 depending upon the amount of contaminants present in the stream, the size of the absorbent module, the particular type of contaminant present in the stream and the absorption properties of the zeolite material 36. The electrical properties through the absorbent module 32 are monitored by the electrical measurement device 46. Changes in the electrical capacitance and/or conductance of absorbent module 32 provide a direct means for measuring the amount of contaminant which is being absorbed.

Capacitance and/or conductance measurements can be made continually to provide detailed information regarding real-time changes in the amounts of contaminants present in the flowing stream of supercritical fluid. Alternatively, capacitance and/or conductance measurements can be made at the beginning and end of a cleaning or extraction process in order to measure the amount of contaminants removed during the cleaning or extraction process. Quantitative measurements of contaminant removal during a cleaning or extraction process is possible by comparing the capacitance and/or conductance measurements to capacitance and/or conductance levels previously obtained for known contaminant concentrations in the supercritical fluid stream.

In many situations, the level of contaminants present in the supercritical fluid may be sufficiently high that one or more absorbent modules will become saturated if the module is exposed to the sampling stream during the entire cleaning or extraction process. In these situations, a plurality of absorbent modules are provided in parallel to allow continual monitoring of contaminant levels in the supercritical fluid. For example, as shown in FIG. 1, during start up of the cleaning or extraction process, valve 22 is closed and valve 20 is open. The sample stream is passed into measurement zone 28 wherein contaminants are absorbed by absorbent module 32. The sample stream, with a reduced contaminant level, is passed back into the main fluid stream through outlet conduit 52. If, during the process, the absorbent module 32 becomes saturated, then valve 20 is closed and valve 22 is opened to redirect the sample stream into measurement vessel 26 where the contaminants are absorbed by module 34. The electrical property through module 34 is then monitored to provide continuous monitoring during the entire process. As is apparent, additional measurement vessels with additional absorbent modules can be provided to allow continual monitoring of a cleaning or extraction process even when relatively large amounts of contaminants may be initially present in the stream of supercritical fluid. When one absorbent module becomes saturated with the contaminant, that module is closed off and the sample stream is directed into a second fresh module. Multiple modules may be used in sequence in this manner. As an option, instead of providing additional measurement vessels and absorbent modules, it is contemplated in accordance with the present invention that the measurement zone which is not actively measuring contaminant levels be opened and the saturated absorbent module be replaced with a fresh absorbent module. The sample stream can then be switched back to the new absorbent module when desired. In this way, continual monitoring of the sample stream can be achieved by switching back and forth between the measurement zones 28 and 30.

Alternatively, zeolites having different pore sizes and/or absorptive properties may be used in parallel in each of the measurement zones to provide for simultaneous measurements of different types of contaminants. This configuration makes it possible to simultaneous monitor a particular cleaning or extraction process for a variety of different contaminants. In another alternative, the different zeolites may each be provided in a separate module and the sample stream is passed through the modules in parallel to simultaneously measure the different contaminants.

Examples of practice are as follows:

A zeolite known to absorb light and heavy hydrocarbons and which belongs to the sodalite family, is commercially available from Linde, being sold as Type 5A. A module of this zeolite material, of cylindrical shape, measuring 0.5 cm in diameter by 2 cm long, has a chemical vapor deposited gold coating on both ends of the cylinder. To these ends, heavy electrical conductors are soldered which feed through insulators for electrical isolation. This entire assembly is encased in a stainless steel vessel with suitable high pressure fittings which are attached to the supercritical fluid cleaning station.

During a typical experiment, the water contained in the system is removed first to avoid false readings, such as by passing the sample stream through a dry stack of zeolite material, as is known in the art. During the monitoring cycle, the zeolite material will fill with the eluted hydrocarbon, such as machining lubricant, and causes the capacitance measured between the two electrodes to increase due to the build-up of the dielectric material. This change in capacitance is monitored until it reaches a maximum and ceases to increase, which indicates the end of the cleaning cycle. Depending on the contamination, one or several modules may have to be switched or valved into the stream, as previously described.

Having thus described exemplary embodiments of the present invention, it should be noted by those skilled in the art that the within disclosures are exemplary only and that various other alternatives, adaptations and modifications may be made within the scope of the present invention. Accordingly, the present invention is not limited to the specific embodiments as illustrated herein, but is only limited by the following claims.

What is claimed is:

1. A system for detecting the presence of contaminants in a supercritical fluid, said system comprising:
   a conduit containing supercritical fluid;
   sampling means connected to said conduit for removing supercritical fluid from said conduit to provide a sample stream;
   a vessel having walls defining a contaminant measurement zone;
   means for introducing said sample stream from said sampling means into said measurement zone;
   an absorbent module comprising an absorbent material located within said measurement zone wherein said absorbent material comprises zeolite and is capable of selectively absorbing contaminants from said sample stream, said absorbent module having an electrical property which varies depending upon the amount of contaminant which is absorbed therein; and
   electrical property measurement means for measuring the electrical property through said absorbent module to thereby provide for detection of contaminants present in said sample stream of supercritical fluid.

2. A system for detecting the presence of contaminants in a supercritical fluid according to claim 1 wherein said zeolite is selected from the group consisting of chabazite, gmelinite, erionite and sodalite.

3. A system for detecting the presence of contaminants in a supercritical fluid according to claim 1 wherein said zeolite has pore sizes of between about 0.5 to 130 angstroms.

4. A system for detecting the presence of contaminants in a supercritical fluid according to claim 1 wherein said absorbent module is in the shape of a rod having two ends wherein an electrode is located at each of said rod ends.

5. A system for detecting the presence of contaminants in a supercritical fluid according to claim 4 wherein said zeolite is selected from the group consisting of chabazite, gmelinite, erionite and sodalite.

6. A system for detecting the presence of contaminants in a supercritical fluid according to claim 4 wherein said zeolite has pore sizes of between about 0.5 and 130 angstroms.

7. A system for detecting the presence of contaminants in a supercritical fluid according to claim 1 wherein a plurality of said vessels are provided having walls defining a plurality of contaminant measurement zones and wherein means are provided for selectively introducing said sample stream into said plurality of measurement zones, wherein each of said measurement zones includes at least one of said absorbent modules located therein, and wherein electrical property measurement means are provided for individually measuring the electrical properties through each of said absorbent modules.

8. A system for detecting the presence of contaminants in a supercritical fluid according to claim 1 wherein a plurality of said absorbent materials are provided to selectively absorb different types of contaminants.

9. A method for detecting the presence of contaminants in supercritical fluid comprising the steps of:
   providing a supercritical fluid;
   contacting a portion of said supercritical fluid with an absorbent material comprising zeolite wherein the absorbent material has an electrical property and wherein the electrical property of said absorbent material varies depending upon the amount of said contaminants absorbed therein; and
   measuring the electrical property of said absorbent material to thereby provide for detection of said contaminants in said supercritical fluid.

10. A method for detecting the presence of contaminants in supercritical fluid according to claim 9 wherein said zeolite is selected from the group consisting of chabazite, gmelinite, erionite and sodalites.

11. A method for detecting the presence of contaminants in supercritical fluid according to claim 9 wherein said zeolite has pore sizes of between about 0.5 to 130 angstroms.

* * * * *